(12) United States Patent
Hargrove et al.

(10) Patent No.: US 9,907,489 B2
(45) Date of Patent: Mar. 6, 2018

(54) SYSTEMS AND METHODS FOR HIERARCHICAL PATTERN RECOGNITION FOR SIMULTANEOUS CONTROL OF MULTIPLE-DEGREE OF FREEDOM MOVEMENTS FOR PROSTHETICS

(71) Applicant: Rehabilitation Institute of Chicago, Chicago, IL (US)

(72) Inventors: Levi Hargrove, Chicago, IL (US); Aaron Young, Chicago, IL (US)

(73) Assignee: Rehabilitation Institute of Chicago, Chicago, IL (US)

(*) Notice: Subject to any disclaimer, the term of this patent is extended or adjusted under 35 U.S.C. 154(b) by 355 days.

(21) Appl. No.: 13/918,418

(22) Filed: Jun. 14, 2013

(65) Prior Publication Data

US 2013/0338540 A1     Dec. 19, 2013

Related U.S. Application Data

(60) Provisional application No. 61/659,887, filed on Jun. 14, 2012.

(51) Int. Cl.
*A61B 5/00* (2006.01)
*A61B 5/0488* (2006.01)
(Continued)

(52) U.S. Cl.
CPC ............ *A61B 5/11* (2013.01); *A61B 5/04888* (2013.01); *A61B 5/7267* (2013.01); *A61F 2/68* (2013.01); *A61F 2/72* (2013.01)

(58) Field of Classification Search
CPC ..... A61F 2/68; A61F 2/72; A61F 4/00; A61B 5/11; A61B 5/1107; A61B 5/1123;
(Continued)

(56) References Cited

U.S. PATENT DOCUMENTS

| 4,209,860 A | 7/1980 | Graupe |
| 4,314,379 A | 2/1982 | Tanie et al. |

(Continued)

FOREIGN PATENT DOCUMENTS

| EP | 1043003 A1 * | 10/2000 | .............. A61F 2/72 |
| WO | WO 2008022435 A1 * | 2/2008 | .............. A61F 2/68 |

OTHER PUBLICATIONS

Derwent abstract of WO2011091399A2) Sun Yan. Jan. 25, 2011.*
(Continued)

*Primary Examiner* — Thomas J Sweet
*Assistant Examiner* — Christie Bahena
(74) *Attorney, Agent, or Firm* — Polsinelli PC; Ari M. Bai

(57) ABSTRACT

This disclosure relates to a hierarchy of classifiers, including linear discriminant analysis (LDA) classifiers, arranged to provide simultaneous control of multiple degrees of freedom of a prosthetic. The high accuracy of the hierarchical approach allows pattern recognition techniques to be extended to permit simultaneous control, potentially allowing amputees to produce more fluid, life-like movements, ultimately increasing their quality of life. The hierarchy may also be used to control a biological interface that allows input to computers for persons with disabilities, used as a potential video-game controller, and used as an input interface for tablets, and phones.

24 Claims, 6 Drawing Sheets

(51) Int. Cl.
  A61F 2/68 (2006.01)
  A61F 2/72 (2006.01)
  A61B 5/11 (2006.01)
(58) Field of Classification Search
  CPC ... A61B 5/1125; A61B 5/6811; A61B 5/6812;
    A61B 5/04888; A61B 5/7267; G06N
    99/005; G06N 99/08; B25J 9/1612
  See application file for complete search history.

(56) References Cited

U.S. PATENT DOCUMENTS

| | | | | |
|---|---|---|---|---|
| 5,336,269 | A * | 8/1994 | Smits | 623/25 |
| 5,673,367 | A * | 9/1997 | Buckley | B25J 9/1612 706/23 |
| 5,888,213 | A | 3/1999 | Sears et al. | |
| 6,171,239 | B1 * | 1/2001 | Humphrey | 600/372 |
| 6,272,479 | B1 * | 8/2001 | Farry et al. | 706/13 |
| 6,679,920 | B2 | 1/2004 | Biedermann et al. | |
| 7,881,780 | B2 | 2/2011 | Flaherty | |
| 7,991,461 | B2 | 8/2011 | Flaherty et al. | |
| 8,060,194 | B2 | 11/2011 | Flaherty | |
| 2003/0176806 | A1 * | 9/2003 | Pineda et al. | 600/544 |
| 2012/0209134 | A1 * | 8/2012 | Morita et al. | 600/546 |
| 2014/0031952 | A1 * | 1/2014 | Harshbarger | A61F 2/72 623/25 |

OTHER PUBLICATIONS

Herle. Myoelectrical signal classification for the hierarchical control of a human hand prosthesis. Automation quality and testing robotics, 2010 IEEE International Conference. May 28-30, 2010.*

Deepthi. A new hierarchical pattern recognition method using mirroring neural networks. 2010 International Journal of Computer Applications. vol. 1—No. 12. 2010.*

Macias, Jose Erazo. Electromyographic pattern analysis and classification for a robotic prosthetic arm. ABBI vol. 3, No. 2, pp. 113-119. 2006.*

Oskoei, Mohammadreza Asghari. Myoelectric control systems—A survey. ScienceDirect. Sep. 2007.*

Hargrove et al, A Comparison of Surface and Intramuscular Myoelectric Signal Classification, IEEE Transactions on Biomedical Engineering, May 2007, vol. 5, No. 5, 847-853.

Hudgins et al, A New Strategy for Multifunciton Myoelectric Control, IEEE Transactions on Biomedical Engineering, Jan. 1993, vol. 40, No. 1, 82-94.

Smith et al, Determining the Optimal Window Length for Pattern Recognition-Based Myoelectric Control: Balancing the Competing Effects of Classification Error and Controller Delay, IEEE Transactions on Neural Systems and Rehabilitation Engineering, Apr. 2011, vol. 19, No. 2, 186-192.

Englehart et al, A Rubust, Real-Time Control Scheme for Multifunction Myoelectric Control, IEEE Transactions on Biomedical Engineering, Jul. 2003, vol. 50, No. 7, 848-854.

Boschmann et al, Development of a Pattern Recognition-Based Myoelectric Transhumeral Prosthesis with Multifunctional Simultaneous Control Using a Model-Driven Approach for Mechatronic Systems, Proceedings of the 2011 MyoElectric Controls/Powered Prosthetics Symposium Frederiction, Aug. 14-19, 2011, New Brunswick Canada.

Baker et al, Continuous Detection and Decoding of Dexterous Finger Flexions with Implantable MyoElectric Sensors, IEEE Transactions on Neural Systems and Rehabilitation Engineering, Aug. 2010, vol. 18, No. 4, 424-432.

Kuiken et al, Targeted Muscle Reinnervation for Real-Time Myoelectric Control of Multifunction Artificial Arms, JAMA 2009; 301(6): 619-628.

Scheme et al, Electromyogram Pattern Recognition for Control of Powered Upper-Limb Prostheses: State of the Art and Challenges for Clinical Use, Journal of Rehabilitation Research and Development, 2011, vol. 48, No. 6, 643-660.

Yatsenko et al, Simultaneous, Proportional, Multi-Axis Prosthesis Control using Multichannel Surface EMG, Proceedings of the 29th Annual Internationial Conference of the IEEE EMBS, Cite Internationale, Lyon, France, Aug. 23-26, 2007, 6133-6136.

Ajiboye et al, Muscle Synergies as a Predictive Framework for the EMG Patterns of New Hand Postures, J Neural Eng., Jun. 2009; 6(3): 1-29.

Jiang et al, Extracting Simultaneous and Proportional Neural Control Information for Multiple-DOF Prostheses from the Surface Electromyographic Signal, IEEE Transactions on Biomedical Engineering, Apr. 2009, vol. 56, No. 4, 1070-1080.

Choi et al, Development of a Myoelectric Joystick: a Preliminary Study, Proceedings of the 2010 3rd IEEE RAS & EMBS International Conference on Biomedical Robotics and Biomechatronics, The University of Tokyo, Tokyo, Japan Sep. 26-29, 2010, 173-178.

Nielsen et al, Simultaneous and Proportional Force Estimation for Multifunction Myoelectric Prostheses Using Mirrored Bilateral Training, IEEE Transactions on Biomedical Engineering, Mar. 2011, vol. 58, No. 3, 681-688.

Muceli et al, Multichannel Surface EMG Based Estimation of Bilateral Hand Kinematics During Movements at Multiple Degrees of Freedom, 32nd Annual International Conference of the IEEE EMBS Buenos Aires, Argentina, Aug. 31-Sep. 4, 2010, 6066-6069.

Kuiken et al, The Use of Targeted Muscle Reinnervation for Improved Myoelectric Prosthesis Control in a Bilateral Shoulder Disarticulation Amputee, Prosthetics and Orthotics International, 2004, 28:245-253.

Kyberd et al, Two-Degree-Of-Freedom Powered Prosthetic Wrist, Journal of Rehabilitation Research & Development, 2011, vol. 48, No. 6, 609-618.

Harris et al, Revolutionizing Prosthetics Software Technology, The Johns Hopkins University Applied Physics Laboratory, Laurel, MD, 2011, 2877-2884.

Resnik, Linda, Research Update: VA Study to Optimize DEKA Arm, Journal of Rehabilitation Research & Development, 2010, vol. 47, No. 3, 9-10.

Miguelez, John M., Clinical Experiences with the Michelangelo Hand, A Four-Year Review, Proceedings of the 2011 MyoElectric Controls/Powered Prosthetics Symposium Fredericton, Aug. 14-19, New Brunswick, Canada.

Waryck, Brian, Comparison of Two Myoelectric Multi-Articulating Prosthetic Hands, Proceedings of the 2011 MyoElectric Controls/ Powered Prosthetics Symposium Fredericton, Aug. 14-19, New Brunswick, Canada.

Van Der Niet Otr, The i-Limb Hand and the DMC Plus Hand Compared: A Case Report, Prosthetics and Orthotics International, 2010, 34:216-220.

Schulz, Stefan, First Experiences with the Vincent Hand, MEC '11 Raising the Standard, Institute of Biomedical Engineering, University of New Brunswick, 283-286.

Medynski et al, Bebionic Prosthetic Design, Proceedings of the 2011 MyoElectric Controls/Powered Prosthetics Symposium Fredericton, Aug. 14-19, 2011, New Brunswick, Canada.

Davidge, Krista, Multifunction Myoelectric Control Using a Linear Electrode Array, Thesis Submitted to The University of New Brunswick, Apr. 2005.

Davidge, Krista, Multifunction Myoelectric Control Using a Linear Electrode Array, Thesis Submitted to the University of New Brunswick, 2005, 97 pages.

* cited by examiner

The Training Algorithm

Training Algorithm for Hierarchical Strategy $DOF \leftarrow \{set\ of\ all\ DOFs\}$
$MC \leftarrow \{set\ of\ discrete\ and\ dual\ combined\ motion\ classes\}$
$M(1:3) \leftarrow \begin{Bmatrix} \{no\ movement\} \\ \{forward\ movement\} \\ \{reverse\ movement\} \end{Bmatrix}$ ⟵ 500 for $l = 1:N_{DOF}$ $TRAIN_{CLASSES}(1:3) = \begin{Bmatrix} \{MC|DOF_l = M(1)\} \\ \{MC|DOF_l = M(2)\} \\ \{MC|DOF_l = M(3)\} \end{Bmatrix}$ $LDA_{WEIGHTS,l,1} = TRAIN_{LDA}(TRAINCLASSES)$ IF $l \neq N_{DOF}$
    $N = 2\ (N_{DOF} - l) + 1$
    $TRAIN_{CLASSES}(1:N) = \{MC|DOF_l = M(2)\}$
    $LDA_{WEIGHTS,l,2} = TRAIN_{LDA}(TRAIN_{CLASSES})$
    $TRAIN_{CLASSES}(1:N) = \{MC|DOF_l = M(3)\}$
    $LDA_{WEIGHTS,l,3} = TRAIN_{LDA}(TRAIN_{CLASSES})$
    $MC = \{MC|DOF_l = M(1)\}$
end
end

FIG. 5

Real-Time Algorithm for Hierarchical Strategy $X \leftarrow$ measurements at each window; $\in R^f$
$OUTPUT_{CLASS(1)} = TEST_{LDA}(xLDA_{WEIGHTS\ 1,1})$
for $l = 1:N_{DOF} - 1$
    IF $OUTPUT_{CLASS(l)} \neq 1$  ⟵ 600
        $OUTPUT_{CLASS(l)} =$
            $TEST_{LDA}(xLDA_{WEIGHTS\ l,OUTPUT\ CLASS(l)})$
        BREAK
    end
    $OUTPUT_{CLASS(l)} = TEST_{LDA}(xLDA_{WEIGHTS\ l+1,1})$
end
RETURN $(OUTPUT_{CLASS})$

FIG. 6

Equations for Hierarchical Control Scheme $\bar{x}$ $\bar{x}$ is the EMG feature vector Equation 1:

Class 1 = arg (p( ) Classes of DOF #1|$\bar{x}$)) ← 700A

Equation 2:

Class 2 = arg (max(p(Classes of DOF #2)|$\bar{x}$, DOF #1 = Class 1)) ← 700B

FIG. 7

SYSTEMS AND METHODS FOR HIERARCHICAL PATTERN RECOGNITION FOR SIMULTANEOUS CONTROL OF MULTIPLE-DEGREE OF FREEDOM MOVEMENTS FOR PROSTHETICS

CROSS REFERENCE TO RELATED APPLICATION

This is a non-provisional patent application that claims benefit to U.S. Provisional Patent Application Ser. No. 61/659,887 filed on Jun. 14, 2012 and is herein incorporated by reference in its entirety.

GOVERNMENT GRANT

This invention was made with government support under contact R01-HD-05-8000 awarded by the National Institutes of Health. The government has certain rights in the invention.

FIELD

This disclosure relates generally to the field of human machine interfaces, and in particular to a system and method of hierarchical pattern recognition for the simultaneous control of multiple-degree of freedom movements for prosthetic devices.

BACKGROUND

Myoelectric prostheses, which rely on electromyography (EMG) signals to control joint movement, are often used to effectively treat upper-limb amputation. The control principles used in commercially available prostheses have been available for many decades and rely on an estimate of the amplitude of strategically placed electrodes coupled with simple rules to form control signals for controlling the operation of the prosthesis. Only a limited number of movements may be restored and to achieve a particular task for movement of the prosthesis, and the movements must be controlled sequentially as only one motion may be controlled at a time.

Pattern recognition has also been used to extract control signals for prosthetic limbs but these algorithms have yet to reach the marketplace. However, pattern recognition myoelectric control is still currently limited to controlling sequential movements, or pre-programmed coordinated movements about several joints in which each joint may not be controlled independently.

Other techniques, which rely on continuous projection of the signal energy onto subspaces, have been used to estimate simultaneous movements of the wrist and hand. The projection matrices have been determined using muscle synergy inspired ideas, or by using neural networks with little a priori information. These methods differ from pattern recognition in which signal patterns are described by multiple features and use methods which partition the feature space.

SUMMARY

The present disclosure relates to a system and method that uses a hierarchical pattern recognition control scheme or control system for classifying both individual and simultaneous movements for multiple degrees of freedom of the prosthesis by interpreting electric potential signals generated by a living subject connected to the prosthesis. The biological signals are first represented by a set of features to extract useful information. Next, the features are presented to a hierarchy of pattern classifiers similar in structure to a decision tree. In the hierarchical scheme, the highest classifier in the hierarchy uses both discrete and combined movement data to determine a movement direction of a single degree of freedom (DOF). The output of this classifier (one of two movement directions or no movement) then determines the next classifier used in the hierarchy. If the output is no movement, then the next classifier is used to determine the movement direction of a second DOF. This second classifier is conditioned on the decision of the first classifier by removing any combined movements involving active motion in the first DOF from the training data set. If, instead, the output of the first DOF is an active movement, then the second classifier used will determine whether the patient intends to make a combined motion. The second classifier which discriminates between the discrete movement selected by the first classifier and all combined motions in which the first motion classified participates. This same pattern is repeated down the hierarchy with one layer for each DOF, where all classifiers lower in the hierarchy are trained using conditioned data. The speed of each movement may be independently estimated using a normalization factor associated with each classifier, thereby allowing the patient to control each movement at a different speed.

In various embodiments, the system and method are suited to extend pattern recognition control of powered neuro-prostheses to allow for combined movements. This system and method may also be used in a variety of applications, such as a biological interface to allow input to computers for other persons with disabilities, as a potential video-game controller, and as an input interface for tablets or phones.

Additional objectives, advantages, and novel features will be set forth in the description which follows or will become apparent to those skilled in the art upon examination of the drawings and detailed description which follows.

BRIEF DESCRIPTION OF THE DRAWINGS

FIG. 5 is an algorithm for training a hierarchical pattern recognition control scheme according to one embodiment;

FIG. 6 is an algorithm for the real-time execution of a hierarchical pattern recognition control scheme according to one embodiment;

FIG. 7 is a general equation for a hierarchical pattern recognition control scheme according to one embodiment.

Corresponding reference characters indicate corresponding elements among the view of the drawings. The headings used in the figures do not limit the scope of the claims.

DETAILED DESCRIPTION

Figure 1:
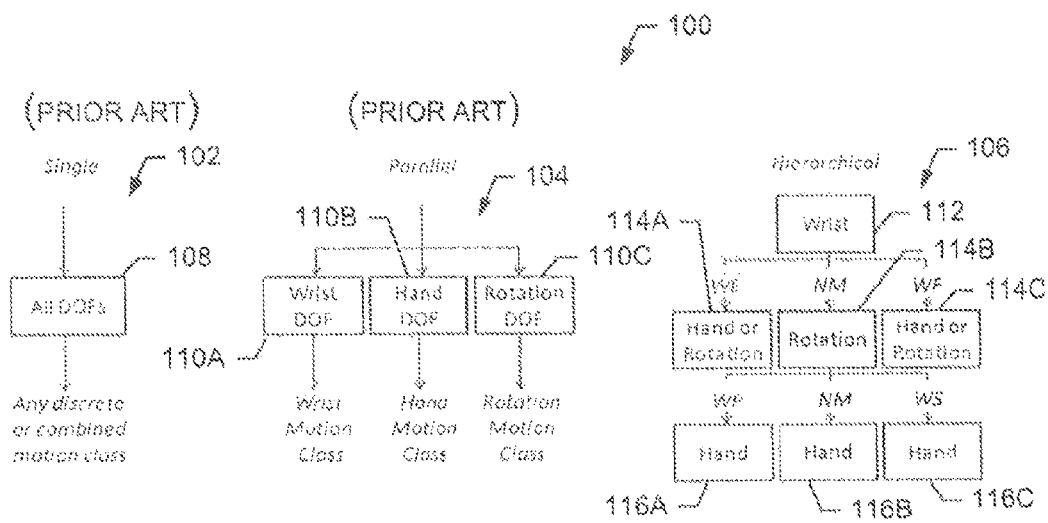
FIG. 1 illustrates a comparison between prior art methods of pattern recognition and a hierarchical pattern recognition control scheme according to one embodiment.

The present disclosure relates to a system and method for the simultaneous control of multiple degrees of freedom for a prosthetic. In particular, the system and method may be used to more accurately classify and control combined joint and/or limb motions for prosthesis. It has been found that simple activities of daily living for a person having a prosthetic, such as opening a door, require simultaneous movement of multiple degrees of freedom (DOF) of the prosthetic. Further, it has been found that pattern recognition imposes fewer restrictions on electrode placements and can provide control information for more prosthetic movements in comparison to conventional amplitude control techniques.

Pattern recognition based algorithms that use surface electromyography (EMG) signals measured from residual muscles show great promise as multi-DOF controllers. Unfortunately, current pattern recognition systems are limited to sequential control of each DOF. The system and method for the simultaneous control of multiple degrees of freedom uses a hierarchy of classifiers, including but not limited to linear discriminant analysis (LDA) classifiers, which are arranged to provide simultaneous DOF control. This approach and two other simultaneous control schemes were evaluated using healthy subjects controlling up to four DOFs, where any two DOFs could be controlled simultaneously. The new hierarchical approach was the most promising with classification errors at or below 15% on average for discrete and combined motions. The classification performance was significantly better (p<0.05) than using a single LDA classifier trained to recognize both discrete and combined motions or classifying each DOF using a set of parallel classifiers. The high accuracy of the hierarchical approach suggests that pattern recognition techniques can be extended to permit simultaneous control, thereby potentially allowing amputees to produce more fluid, life-like movements with the prosthetic and ultimately enhancing their quality of life.

In various embodiments, the systems and methods as described herein are suited to execute pattern recognition control of powered neuro-prostheses to allow for combined movements. These systems and methods also have applications for uses as a biological interface to allow input to computers for other persons with disabilities, as a potential video-game controller, and as an input interface for tablets or phones.

In the hierarchical control scheme, the highest classifier in the hierarchy uses both discrete and combined motion data to determine a motion class for a single DOF. The output of this classifier (one of two active motion classes or no motion) then determines the next classifier used in the hierarchy. If the output is no motion, then the next classifier is used to determine the motion class of a second DOF. This second classifier is conditioned on the decision of the first classifier by removing any combined movements involving active motion in the first DOF from a training data set. If, instead, the output of the first DOF is an active motion class, then the second classifier used will determine whether the current intent is a combined motion. The second classifier used is a single LDA classifier which discriminates between the discrete motion selected by the first classifier and all combined motions in which the first motion classified participates. This same pattern is repeated down the hierarchy with one layer for each DOF such that all classifiers lower in the hierarchy are trained using data conditioned.

In various embodiments, the systems and methods of hierarchical pattern recognition system use a hierarchical-based control scheme for classifying combined motions of a user. FIG. 1 depicts a comparison 100 between two prior art methods of pattern recognition 102 and 104 and the hierarchical pattern recognition control scheme 106 for a three DOF controller. Previously used approaches include a single LDA classification control scheme 102 and a parallel classification control scheme 104. Each control scheme 102, 104 and 106 receives input or data related to EMG signals and outputs data or a signal for controlling a prosthetic device.

The single LDA classification control scheme 102 of the prior art uses one LDA classifier 108 and discriminates all discrete and combined motion classes as separate motions for all DOFs. The single LDA classification control scheme 102 outputs a separate signal for each separate motion.

Similarly, the parallel classification control scheme 104 of the prior art discriminates each DOF individually by using three LDA classifiers 110A-C. In the parallel classification control scheme 104, the decision regarding the motion of each classifier 110A-C is calculated independently. Further, each classifier 110A-C consists of three motion classes: the two opposing motion classes of a DOF (e.g. flexion and extension) and no motion. Each motion class is trained using data from its discrete motion and all combined motions, which include the discrete motion. The parallel classification control scheme 104 then outputs a signal for a combined movement when outputs for two of the classifiers 110A-C correspond to active motion classes. The parallel classification control scheme 104 is distinguished from the hierarchical classification control scheme 106 in that combined motions are not used to train a parallel classification control scheme.

The hierarchical classification control scheme 106 uses the output of DOFs 112 or 114A-C higher in the hierarchy to choose classifiers for DOFs lower in the hierarchy 114A-C or 116A-C, respectively. As an example, first the wrist DOF motion is classified at the wrist DOF classifier 112. The output, which may be wrist flexion (WF), wrist extension (WE), or no motion (NM), is used to choose the second LDA classifier 114A-C. If the wrist is not moving, a classifier 114B for just rotation is used and its output determines which of three hand DOF classifiers 116A-C to use. If the wrist is moving (e.g. WF or WE), a classifier 114A or 114B that identifies all remaining discrete motion classes (wrist pronation (WP), wrist supination (WS), hand open, hand closed, or NM is used to choose if a second motion class is active.

Figure 2:
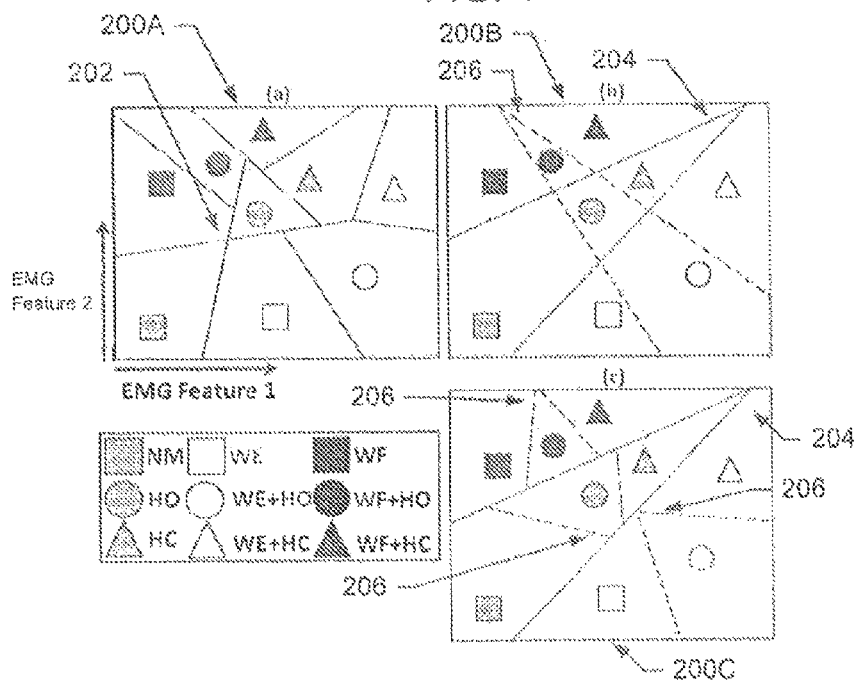
FIG. 2 depicts feature spaces to illustrate boundary sets for each control scheme according to one embodiment.

FIG. 2 illustrates feature spaces 200A-C for the three control schemes 102-106, respectively, to illustrate the various boundary sets for each control scheme in a two DOF configuration that may be used to discriminate between motion classes. The single LDA classifier control scheme 102 separates in one step each discrete and combined motion as individual classes, indicated generally as 202. In the parallel classifier control scheme 104, the LDA classifier for each DOF produces a boundary for wrist motions 204 and boundary for hand motions 206 for its three motion classes. The union of the boundaries 204-206 for all DOFs produces the overall classification boundaries for parallel classifier control scheme 104. Combined motions result when features can be mapped to active motions within both of the boundaries 204 and 206.

The boundary for wrist motions 204 and boundary for hand motions 206 in the hierarchical classifier control scheme 106 progressively separate the feature space 200 as one navigates down the hierarchy. The feature space is first partitioned for the first DOF (i.e. wrist motions) by the boundary for wrist motions 204 in the same manner as the parallel classifier control scheme 104. The classifiers of the second DOF (i.e. hand motions) then derive the boundaries for hand motion 206 based on the boundaries formed by the classifier for the first DOF.

Figure 3A:
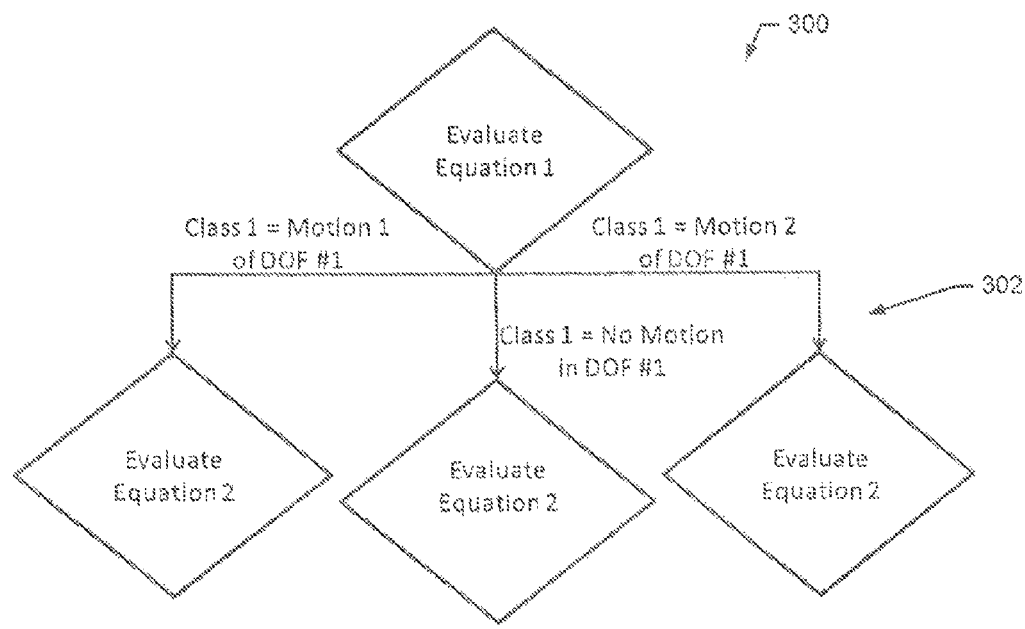
FIG. 3A depicts a flowchart of a simplified hierarchical control scheme according to one embodiment.

FIG. 3A depicts a flowchart of a simplified hierarchical control scheme for two degrees of freedom. As shown, each additional layer of the hierarchy 300 for more than two DOFs is substantially similar to the second layer 302 and conditioned on all layers higher in the hierarchy.

Figure 3B:
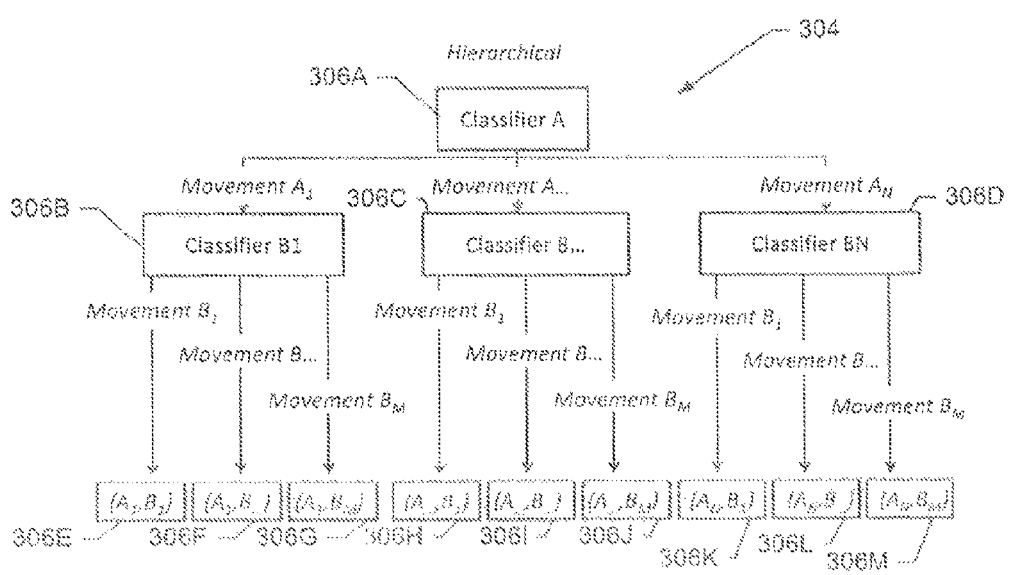
FIG. 3B depicts a flowchart of a generic representation of a two-level hierarchy according to one embodiment.

FIG. 3B depicts generic representation of a two-level hierarchy 304. The inputs to each classifier 306A-M are features or a subset of the features extracted from one or more EMG signals. In various embodiments of the hierarchical control scheme 106, the movement groupings may be determined automatically using clustering, or by evaluating the classification accuracy using a test set of data, or manually using trial and error.

Figure 4A:
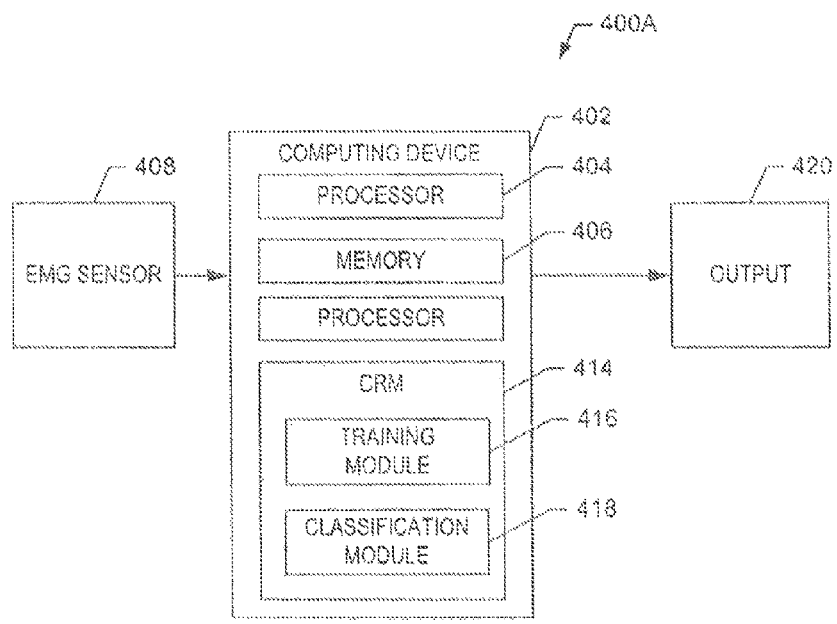
FIGS. 4A and 4B depict embodiments of systems that may be used for performing training and executing the hierarchical pattern recognition control scheme.
Figure 4B:
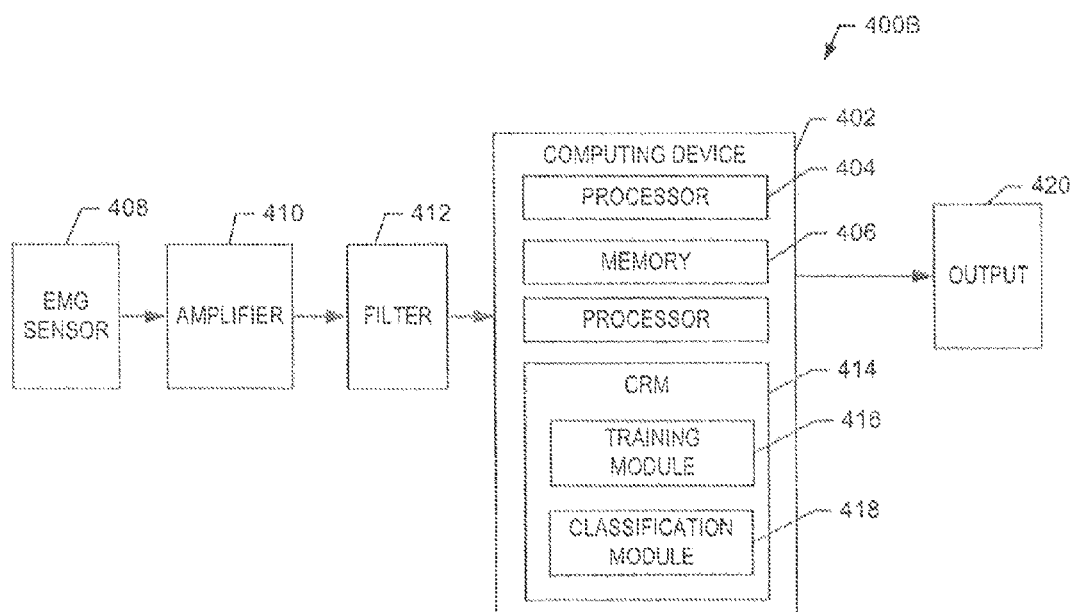

Referring now to FIGS. 4A and 4B, embodiments of systems that may be used for performing training and executing the hierarchical pattern recognition control scheme are shown and indicated generally as 400A and 400B, respectively.

In one embodiment, the system 400A includes a computing device 402. The computing device 402 includes at least one processor 404 and memory 406. For example, the computing device 402 may be a personal computer, workstation, server, or mobile device. The processor 404 is a hardware device that processes software, other machine-readable instructions, retrieved data, and/or received data. The memory 406 may store the software or other machine-readable instructions and data. The memory 406 may include volatile and/or non-volatile memory. The memory 406 may comprise a database to store data related to parameters for various components of system 400A or 400B, one or more prosthetic devices, one or EMG signal patterns, various DOFs, or any other data. The computing device 402 may further include various hardware and accompanying software components, such as a signal amplifier 410 or a signal filter 412, that may be configured for receiving EMG signal data from one or more EMG sensors 408 and generating an output 420 that may be received at a display or a prosthetic device, among others.

Additionally, the computing device 402 may also include a communication system to communicate with one or more components of the systems 400A and 400B and optionally other sensors and/or computing devices and systems, over a communication network via wireline and/or wireless communications, such as through the Internet, an intranet, and Ethernet network, a wireline network, a wireless network. The computing device 402 may further include a display (not shown) for viewing data or one or more user interfaces (UI), such as a computer monitor, and an input device (not shown), such as a keyboard or a pointing device (e.g., a mouse, trackball, pen, touch pad, or other device) for entering data and navigating through data, including images, documents, structured data, unstructured data, HTML pages, other web pages, and other data.

The computing device 402 may include a database (not shown) and/or is configured to access the database. The database may be a general repository of data including, but not limited to user data, patient data, historical training data, or algorithms, among others. The database may include memory and one or more processors or processing systems to receive, process, query and transmit communications and store and retrieve such data. In another aspect, the database may be a database server.

According to one aspect, the computing device 402 includes a computer readable medium ("CRM") 414, which may include computer storage media, communication media, and/or another available media medium that can be accessed by the processor 404. For example, CRM 414 may include non-transient computer storage media and communication media. By way of example and not limitation, computer storage media includes memory, volatile media, nonvolatile media, removable media, and/or non-removable media implemented in a method or technology for storage of information, such as machine/computer readable/executable instructions, data structures, program modules, or other data. Communication media includes machine/computer readable/executable instructions, data structures, program modules, or other data and includes an information delivery media or system. Generally, program modules include routines, programs, instructions, objects, components, data structures, etc., that perform particular tasks or implement particular abstract data type By way of example and not limitation, the CRM 414 may store executable instructions to execute a hierarchical pattern recognition training algorithm at a training module 416 or a real-time hierarchical pattern recognition control scheme algorithm and a classification module 418. FIG. 5 provides an example hierarchical pattern recognition training algorithm 500 that may be executed by the system 400A or 400B. One or more other hierarchical pattern recognition training algorithms may also be used. Similarly, FIG. 6 provides an example real-time hierarchical pattern recognition control scheme algorithm 600, although one or more other real-time hierarchical pattern recognition control scheme algorithms may be used. FIG. 7 provides example equations 700A and 700B for a hierarchical control scheme.

In various embodiments, the training and execution of the hierarchical pattern recognition control scheme may be performed on a processing device incorporated with, in close proximity to, or otherwise in communication with a prosthetic device worn by a patient. Alternately, data related to the training and execution of the hierarchical pattern recognition control scheme may be transferred to a processor and/or memory incorporated with, in close proximity to, or otherwise in communication with a prosthetic device worn by a patient.

Exemplary Method of Training and Classifying Motions

In one example, six healthy subjects (three males and three females) were used to train and test a hierarchical pattern recognition control scheme. Four pairs of electrodes were placed around the circumference of the upper forearm approximately 2 cm distal to the elbow such that two pairs were placed on the wrist flexor muscle group and two pairs were placed on the wrist extensor muscle group. Two additional pairs of electrodes were also placed on the biceps and triceps to provide elbow discrimination. A ground electrode was placed on the olecranon, but positioned away from the muscles of interest.

EMG data was collected using a Bagnoli-16 Amplifier manufactured by Delsys of Boston, Mass. The EMG signals were amplified to a convenient value using a computing device executing Matlab by MathWorks of Natick, Mass. The EMG signals were digitally sampled at 1000 Hz and high pass filtered at 20 Hz using a 3rd order Butterworth filter to reduce motion artifact.

Motions collected were hand open/close (HO/HC), wrist extension/flexion (WE/WF), wrist supination/pronation (WS/WP), elbow extension/flexion (EE/EF), no motion (NM) and all two DOF combined motions. Combined motions involving greater than two DOFs were not trained due to subjects reporting difficulty in visualizing such complex motions during pilot data collection, and the impracticality of collecting training data for every combined motion involving more than two DOFs. The data collection sessions were guided using visual prompts from custom designed software.

The subjects were instructed to make medium, constant force contractions to the best of their ability; however, no feedback was provided to the subjects during the data collection procedure. Ample rest periods were provided during the data collection process to prevent fatigue.

EMG data were divided into 250 ms windows with 50 ms frame increment and were represented using time domain (TD) features. Four-fold cross validation was used to train and test each control scheme.

For each of the three classification control schemes 102, 104 and 106, three different DOF configurations were tested as shown in Table 1 below.

TABLE I

DOFS AND AMOUNT OF DATA COLLECTED FOR EACH SUBJECT

| Number of DOFs | Motions | Amount of Data |
|---|---|---|
| 2 | HO/HC, WE/WF | 108 s (12 s per class)* |
| 3 | HO/HC, WE/WF, WS/WP | 228 s (12 s per class)* |
| 4 | HO/HC, WE/WF, WS/WP, EE/EF | 396 s (12 s per class)* |

*Classes include discrete motions, combined motions, and no motion.

The control schemes 102, 104 and 106 controlled the discrete motions for each available DOF and all combined motions where only two DOFs were activated simultaneously. The two DOF configuration consisted of eight motion classes in which four were discrete and four were combined motion classes. The three DOF configuration consisted of fourteen motion classes in which six were discrete and eight were combined motion classes. The four DOF configuration consisted of eight discrete motions and twenty combined motion classes.

The two and three DOF configurations used only the four channels around the forearm to provide EMG signals. However, with the addition of elbow flexion/extension in the four DOF configuration, two additional channels were used to include biceps and triceps activity. For all classification control schemes 102, 104 and 106, all available channels were used for every classification decision.

For the parallel classification control scheme 104, the output of the three and four DOF configurations was limited to produce only the two active motion classes that had the highest probability of correctness. This constraint was only necessary during less than 5% of all classifications.

For the hierarchical control scheme 106, the order of the DOFs in the hierarchy was chosen to ensure the best possible order for each user. This ordering of DOFs was tuned to each individual subject by evaluating performance on a test set of data for every possible ordering.

In various embodiments, the speed at which the movement is controlled is often related to the amplitude feature of the EMG signal and is referred to as proportional control. The speed of the movement is controlled using a linear combination of the EMG features. The linear combination of the features is computed automatically using an algorithm such as, but not limited to principal components analysis, independent component analysis, or linear discriminant analysis (LDA) that interprets training data used to create each classifier. The linear combination may be furthermore modified by making manual adjustments via a gain, or threshold to further refine the speed for each movement if necessary. As a result, each classifier provides a movement speed estimate that is applied if the movement was classified as active by the classifier.

Evaluating the Control Schemes

After training the control schemes 102, 104 and 106, offline classification error, defined as the percent of incorrect classifications, was used to evaluate classifier performances. For each control scheme 102, 104 and 106, the classification error resulting from testing discrete motions and combined motions were also reported. Statistical comparisons were conducted using a general linear model with classification error as the response variable, DOF configuration, classifier control scheme, error type (discrete or combined) as fixed factors, and subject as a random factor. Post-hoc comparisons with a Bonferroni correction factor were conducted to analyze differences between classifier control scheme, DOF configurations, and error type.

The single, parallel, and hierarchical classifier control schemes 102, 104 and 106, respectively, are effectively combined motion control schemes. As such, a sequential LDA classifier control scheme (not shown) was also trained on the discrete motion classes. The performance of the sequential LDA classifier control scheme is compared to the discrete motion classification error of the combined motion classification schemes 102, 104 and 106.

Figure 8A:
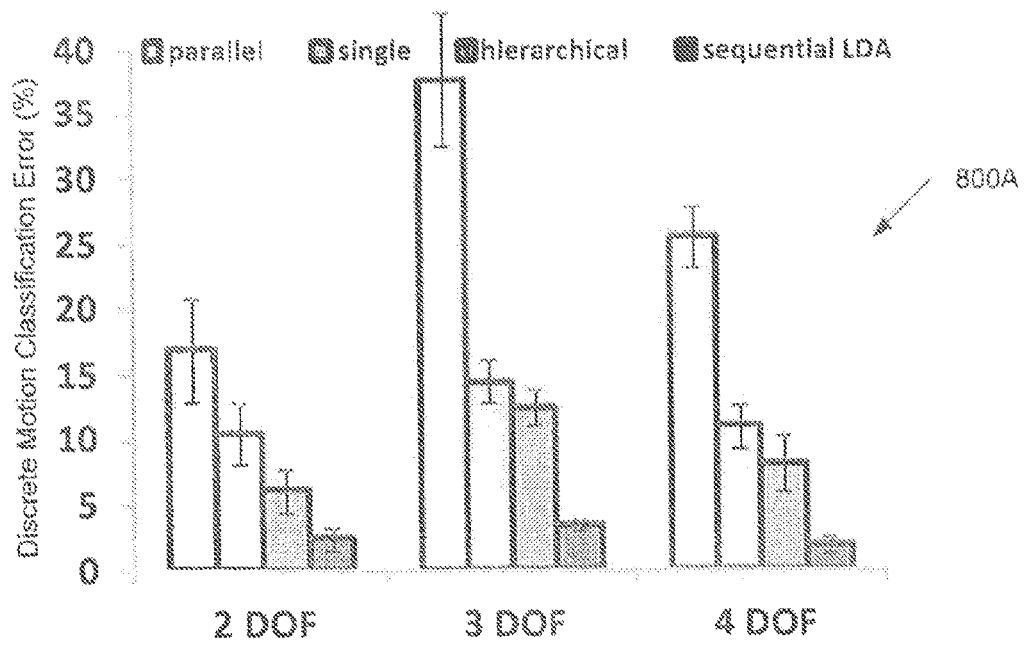
FIGS. 8A and 8B depict graphs of the discrete motion classification error for all control schemes of the combined motion classification error for the three combined motion control schemes, respectively.
Figure 8B:
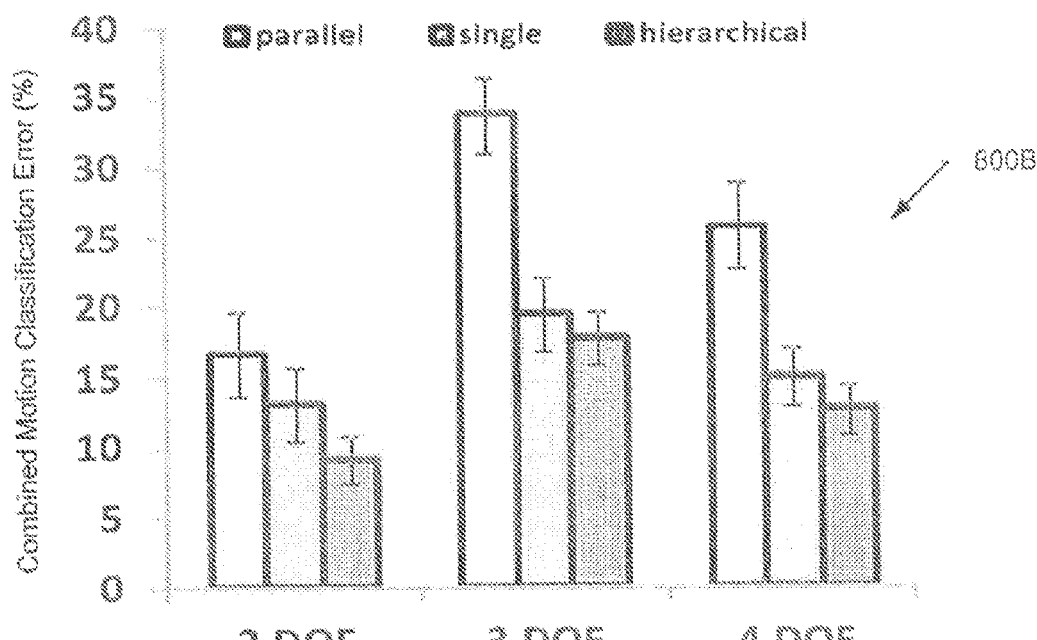

Referring now to FIGS. 8A and 8B, a graph 800A illustrates the discrete motion classification error for all control schemes and a graph 800B showing the combined motion classification error of the three combined motion control schemes 102, 104 and 106 for various DOFs are shown. The results are an average across the six subjects. Error bars show +/−1 SEM. As shown, the type of classifier control scheme and the number of DOFs controlled significantly affected overall classification error ($p<0.01$ for both). In the post-hoc test, the single and the hierarchical control schemes 102 and 106, respectively, performed better than the parallel control scheme 104 ($p<0.01$). The hierarchical classifier control scheme 106 performed better than the single classifier control scheme 102 ($p<0.05$). The two DOF configurations performed better than the three DOF or four DOF configurations ($p<0.01$), and the four DOF configuration performed significantly better ($p<0.01$) than the three DOF configuration. For discrete motions, the standard sequential classifier outperformed all the combined motion classifier control schemes 102, 104 and 106 ($p<0.01$ for all control schemes). As shown, the classification error for discrete movements, as shown in FIG. 8A was found to be significantly better ($p<0.05$) than the classification error for combined movements, as shown in FIG. 8B.

Classification errors for each of the classifiers in the parallel control scheme 104 are displayed in Table below. Further analysis shows that the hand open/close DOF had the highest error for all DOF configurations.

TABLE II

CLASSIFICATION ERROR (%) FOR EACH DOF IN PARALLEL CONTROL SCHEME

| Number of DOFS | Wrist DOF | Hand DOF | Rotation DOF | Elbow DOF |
|---|---|---|---|---|
| 2 | 2.2 ± 0.5 | 14.3 ± 2.7 | — | — |
| 3 | 10.5 ± 1.1 | 25.9 ± 2.8 | 12.6 ± 2.7 | — |
| 4 | 20.7 ± 3.6 | 29.3 ± 2.8 | 21.1 ± 1.9 | 9.5 ± 2.2 |

± indicates standard error of the mean

The hierarchical pattern recognition control scheme 106 had significantly lower classification error performance in comparison with other methods and the average classification error was than 10%. Previous experience testing pattern recognition myoelectric control systems (without the ability to control simultaneous movements) show that errors rates of this magnitude yield clinically viable control systems. The subjects also successfully demonstrated excellent real-time control within the virtual environment and were able to confirm the virtual prosthesis into postures more quickly using a control system with control over simultaneous movements, in comparison to a system the allowed only control over discrete movements. The subjects also demonstrated the ability to move individual movements and combined movements at speeds proportional to the intensity of their muscle contractions.

The hierarchical control scheme 106 not only achieved an overall classification error of 15% or less for each DOF configuration tested for discrete and combined motions, but also showed the lowest discrete motion classification error of the three methods tested, as shown in FIG. 8A.

The results presented of the comparison identify characteristics of classifier architecture for discriminating the investigated motions. The training accuracies in the single classification scheme 102 were high (94% for the two DOF configuration, 92% for the three DOF configuration, and 93% for the four DOF configuration). This suggests that it is possible to linearly separate the discrete and combined motions. This is consistent with previous efforts that have shown linear classifiers to perform as well as more complex nonlinear control systems in discriminating motion classes. Each of the three classification schemes 102, 104 and 106 presented used linear boundaries to discriminate between motion classes, as shown in FIG. 2, yet produced significantly different classification performances (p<0.05). The classification scheme with the lowest classification error was the hierarchical control scheme 106, which outperformed both the single control scheme 104 and the parallel control scheme 106.

The single LDA classifier control scheme 102 makes no assumptions on how classes are grouped in feature space, and therefore treats single motion and combined motion classes equally when calculating classification boundaries. The entire set of training data is used to calculate $2N_{DOF}^2$ boundaries to partition $2N_{DOF}^2+1$ classes (where $N_{DOF}$ equals the number of DOFs available in the control scheme). T In contrast, the parallel control scheme 104 assumes that motion classes that share at least one active DOF motion (e.g. WF, WF/HO, and WF/HC for a 2 DOF configuration) will be well separated in feature space. The parallel control scheme 104 also assumes that these groupings will be linearly separable from the grouping for the antagonistic movement (e.g. WE, WE/HO, and WE/HC) and grouping for no motion in that DOF (e.g. NM, HO, and HC). The overall poorer performance of the parallel method suggests that this assumption is not always valid. In particular the classification accuracies for each DOF classifier in the parallel control scheme 104 demonstrate that while some DOFs may be well discriminated by this assumption (well-separable DOFs), others, such as the hand DOF, are not (less-separable DOFs). The assumptions made with the parallel control scheme 104 have implications on the number of classification boundaries calculated, as only $2N_{DOF}$ linear boundaries to separate $2N_{DOF}^2$ classes. Therefore, as the number of degrees of freedom increases, the total number of motion classes quickly surpasses the number of boundaries the parallel control scheme 104 calculates to separate these classes. This disparity between the number of classes and number of boundaries is not true for the single LDA control scheme 102 or the hierarchical control scheme 106 (which both produce $2N_{DOF}^2$ boundaries), and may explain the substantial increases in classification error produced by the parallel method with higher numbers of DOFs.

Despite the poorer performance of the parallel control scheme 104, the success of hierarchical control scheme 106 suggests that using groups of similar motions for classification may be advantageous, if groupings are applied appropriately. The hierarchical control scheme 106 uses the output of classifiers that group motions within more-separable DOFs (higher on the hierarchy) to choose more optimal classifiers for discriminating between the classes of less-separable DOFs (lower on the hierarchy). As a result, the hierarchy of LDA classifiers produces $2N_{DOF}^2$ classification boundaries that are specifically intended to better separate motions that share a similar DOF activation.

Given that decisions lower on the hierarchy are conditioned by decisions made higher in the hierarchy, it is also desired that the error of the earlier decisions be minimized. Because DOFs evaluated earlier in the hierarchy include more motion classes in the groupings, DOFs should be arranged where more-separable DOFs are evaluated before the less-separable DOFs.

The hierarchical and other combined motion control schemes at each of the DOF configurations investigated may provide simultaneous control of up to two DOFs for a variety of amputation levels and prostheses types. Both the two DOF and the three DOF controllers are applicable to transradial amputees that use a myoelectric prosthesis to control both hand movements and wrist movements (WF/WE and/or WP/WS). The successful classification of combined wrist/hand movements is desirous, given the lack of significant prior efforts for controlling wrist and hand motions simultaneously. The three DOF controller studied allows for control of emerging advanced arms that allow two DOF wrist motion. In addition, the four DOF configuration, which adds elbow flexion/extension control in combination with any wrist or hand movement, suggests that the hierarchical control scheme may be used by transhumeral and shoulder disarticulation amputees who have undergone TMR surgery. Control of elbow movement is an important functional capability for this patient population. The parallel scheme's ability to classify elbow motions with simultaneous control of other DOFs is therefore a promising result. It is interesting to note the decrease in classification error in the four DOF configuration compared to the three DOF configuration. This occurred because the discrete and combined motions involving the elbow joint were easily discriminated by each of the combined motions classification control schemes, thereby decreasing the overall classification error for the four DOF configurations.

It is also useful to note that, the hierarchical control scheme 106 may be expanded to control advanced hands entering the market, as different hand grasp patterns can be incorporated as subclasses of the hand close motion class. In various embodiments, other approaches, such as the use of muscle synergies may also prove beneficial for simultaneous pattern recognition control to reduce the amount of training data needed.

The examples disclosed herein should be construed in any way to limit the scope of the invention. The hierarchical control scheme 106 may be generalized to support classifiers other than the LDA classifier. The features extracted when using the hierarchical control scheme 106 may also be extended to other features for myoelectric control.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A biological interface system comprising:
    a sensor comprising a plurality of electrodes for detecting a multi-cellular potential emanating from one or more living cells of a subject; and
    a processing device comprising a processor and memory to extract features from the multi-cellular potential, wherein the processing device determines an intended movement of a prosthesis based on a hierarchical pattern recognition control scheme executing on the processor,
    wherein the hierarchical pattern recognition control scheme comprises:
        a first classifier configured to determine an intended motion of the prosthesis within a first degree of freedom of the prosthesis and to produce an output reflecting the intended motion; and
        a plurality of subsequent classifiers,
    wherein the hierarchical pattern recognition control scheme is configured to:
        select a second classifier from the plurality of subsequent classifiers on the basis of the output of the first classifier reflecting the intended motion; and
        use the second classifier to determine an intended motion of the prosthesis within a second degree of freedom of the prosthesis;
    wherein the processing device is configured to send the intended movement to the prosthesis for control of the prosthesis.

2. The system of claim 1, wherein each of the subsequent classifiers is defined by a degree of freedom of the prosthesis for a domain of possible joint movements.

3. The system of claim 2, wherein subsequent classifiers are for a domain of possible joint movements that comprises simultaneous combinations of a set of independent movements about a single joint of the prosthesis.

4. The system of claim 2, wherein each of the plurality of hierarchy pattern classifiers or a subset of the plurality of hierarchical pattern classifiers is conditionally dependent.

5. The system of claim 1, wherein the multi-cellular potential is an electromyographic signal.

6. The system of claim 1, further comprising an output unit to send the commands to a prosthetic limb for real-time control of the prosthetic limb.

7. The system of claim 1, further comprising a controller interface, wherein the processing device further comprises an output unit to send commands to the controller interface.

8. The system of claim 7, wherein the controller interface is selected from a group consisting of a computer, a cell phone, computer tables, and video games.

9. The system of claim 1, wherein the hierarchical pattern recognition system has been trained using training data collected from a set of single joint movements, preprogrammed joint movements, or a combination thereof.

10. The system of claim 1, wherein the organization of a hierarchy of the hierarchical pattern recognition system is determined by evaluating with a processing device a classification accuracy using a set of testing data.

11. The system of claim 10, wherein an organization of the hierarchy is determined using at least one clustering algorithm.

12. The system of claim 10, wherein at least one feature is used as an input to each classifier in the hierarchy.

13. The system of claim 12, wherein the selection of the at least one feature is determined by evaluating with a processing device the classification accuracy using a testing set of data.

14. The system of claim 12, wherein the selection of the at least one feature is determined by evaluating with a processing device the classification accuracy using at least one clustering algorithm.

15. The system of claim 1, wherein the first degree of freedom of the prosthesis is a wrist flexion/extension degree of freedom.

16. The system of claim 1, wherein the second degree of freedom of the prosthesis is a wrist pronation/supination degree of freedom.

17. The system of claim 1, wherein the hierarchical pattern recognition control scheme is further configured to:
    select a third classifier from the plurality of subsequent classifiers on the basis of an output of the second classifier that reflects the intended motion of the prosthesis within the second degree of freedom; and
    use the third classifier to determine an intended motion of the prosthesis within a third degree of freedom of the prosthesis.

18. The system of claim 17, wherein the third degree of freedom of the prosthesis is a hand open/close degree of freedom.

19. The system of claim 1, wherein the output of the first classifier reflects an output selected from the group consisting of no intended motion within the first degree of freedom, a motion in a first direction within the first degree of freedom, and a motion in a second direction within the first degree of freedom.

20. The system of claim 1, wherein the hierarchical pattern recognition control scheme is further configured such that if the output of the first classifier reflects no intended motion in the first degree of freedom, then the second classifier selected is one that is conditioned on a training data set that does not include combined movements involving an active motion in the first degree of freedom.

21. The system of claim 20, wherein the hierarchical pattern recognition control scheme is further configured such that if the output of the first classifier reflects active motion in the first degree of freedom, then the second classifier selected is configured to distinguish between an active motion solely in the first degree of freedom and at least one other combined motion that includes the active motion.

22. The system of claim 1, wherein the hierarchical pattern recognition control scheme is further configured such that if the output of the first classifier reflects active motion in the first degree of freedom, then the second classifier selected is configured to distinguish between an active motion solely in the first degree of freedom and at least one other combined motion that includes the active motion.

23. The system of claim 1, wherein the prosthesis is an artificial prosthesis for replacement of at least a portion of a human limb.

24. The system of claim 1, wherein the prosthesis is a virtual prosthesis displayed on a screen.

* * * * *